United States Patent [19]

Larson

[11] E Re. 30,541

[45] Reissued * Mar. 10, 1981

[54] THERMOPLASTIC SPLINT OR CAST

[76] Inventor: Lester M. Larson, 4619 Bailey Dr., Wilmington, Del. 19808

[ * ] Notice: The portion of the term of this patent subsequent to Jan. 20, 1987, has been disclaimed.

[21] Appl. No.: 741,521

[22] Filed: Nov. 12, 1976

Related U.S. Patent Documents

Reissue of:

[64] Patent No.: 3,853,124
Issued: Dec. 10, 1974
Appl. No.: 305,914
Filed: Nov. 13, 1972

U.S. Applications:

[63] Continuation-in-part of Ser. No. 3,474, Jan. 16, 1970, Pat. No. 3,809,600, which is a continuation-in-part of Ser. No. 683,016, Nov. 4, 1967, Pat. No. 3,490,444.

[51] Int. Cl.[3] ..... A61F 5/04
[52] U.S. Cl. ..... 128/90
[58] Field of Search ..... 128/90, 89 R; 161/109, 161/112, 113; 260/17.4 BB; 264/222

[56] References Cited

U.S. PATENT DOCUMENTS

| | | | |
|---|---|---|---|
| 2,616,418 | 11/1952 | Eberl | 128/90 |
| 2,800,129 | 7/1957 | Van Swaay | 128/90 |
| 3,176,685 | 4/1965 | Smarook | 128/90 |
| 3,314,419 | 4/1967 | Quick | 128/90 |
| 3,490,444 | 1/1970 | Larson | 128/90 |
| 3,502,747 | 3/1970 | Fischer et al. | 260/894 |
| 3,585,639 | 6/1971 | Enicks | 128/90 X |
| 3,656,476 | 4/1972 | Swinney | 128/90 |
| 3,662,057 | 5/1972 | Webster et al. | 128/90 X |
| 3,692,023 | 9/1972 | Phillips et al. | 128/90 |
| 3,728,206 | 4/1973 | Buese | 128/90 X |
| 3,819,796 | 6/1974 | Webster et al. | 128/90 X |

FOREIGN PATENT DOCUMENTS

| | | | |
|---|---|---|---|
| 746291 | 11/1966 | Canada | 128/90 |

OTHER PUBLICATIONS

"Splinting with a New Thermoplastic Material", Fried et al., Physical Therapy, vol. 47, No. 12, 1967.

"New Product Makes Splinting Easier", A.J.O.T., XX, 1, 1966.

*Primary Examiner*—John D. Yasko
*Attorney, Agent, or Firm*—Geoffrey R. Myers

[57] ABSTRACT

Polydiene sheet material useful as a body supporting member such as a cast or splint, heat softenable at a higher than body temperature, but slowly recrystallizable or hardenable below about 40° C., treated by distributing throughout the substance small pores, perforations or surface irregularities as by foaming all or only one surface portion of the sheet material, particularly texturing, knurling, pocking or cratering the surface to be placed adjacent to the body member to be encased to allow moisture and/or air transfer away from the enclosed body surface.

6 Claims, 10 Drawing Figures

THE TEMPERATURE-HARDNESS RELATIONSHIP OF POLYMER SOFTENED WITH MINIMAL HEAT RATE = ±2° C/MIN.
TRANSPOLYISOPRENE HEATING AND COOLING

THE TEMPERATURE-HARDNESS RELATIONSHIP OF POLYMER SOFTENED WITH EXCESS HEAT RATE = ±2° C/MIN.
TRANSPOLYISOPRENE HEATING AND COOLING

THERMOPLASTIC SPLINT OR CAST

Matter enclosed in heavy brackets [ ] appears in the original patent but forms no part of this reissue specification; matter printed in italics indicates the additions made by reissue.

This invention is a continuation-in-part of my copending application, Ser. No. 3,474, filed Jan. 16, 1970, and now U.S. Pat. No. 3,809,600, in turn a continuation-in-part of my copending application, Ser. No. 683,016, filed Nov. 4, 1967, now U.S. Pat. No. 3,490,444.

This invention relates to improved processes for forming body supporting casts or splints from thermoplastic sheets and tapes which are moldable to desired body supporting shape when softened by heat above the critical crystalline melting point and held there for a sufficient time to become moldably soft, the plastic returning to its crystalline hardness upon cooling, the plastics hereof upon softening developing a hysteresis which allows the plastic to pass through the crystalline melting point upon cooling to a temperature well below that point such as below a comfortable body temperature to remain soft and pliable, thereby allowing easy application to the body at a comfortable temperature. The softened plastic then hardens in a reasonable time at the lower temperature to set to a hard crystalline polymer substance in body support form.

More particularly, this invention is directed to using certain polydienes, typically transpolyisoprene or transpolychlorene, as plastic substances in sheet or tape form, or other suitable form for use as a body supporting cast or splint, by heating the polymer well above its crystalline transition point such as above 65° C. and, more practically, usually up to the boiling point of water for a period long enough to thoroughly soften the plastic material and to overcome by heating all crystalline portions of the plastic body thoroughly and then cooling the heated plastic down to a comfortable body temperature such as about 45° C. or less, and then applying the softened plastic material to the body member to be protected as a cast or splint, holding the encased body member for an additional period until the splint material hardens and sets by crystallization.

This invention further provides surface irregularities, perforations or a porous texture upon at least the surface upon the sheet material adapted to lie adjacent to the body part to be encased by the sheath or splint which is made porous.

In a prior invention, Canadian Pat. No. 746,291, dated Nov. 15, 1966, whose substance is here incorporated by reference, certain polydienes, typically transpolyisoprene such as natural balata essentially freed of natural resins by precipitation, its synthetic form transpolyisoprene, as well as low temperature polymerized polychloroprene are shown to be useful plastic substances in sheet or tape form for forming body member supporting casts and splints. It was proposed in my prior patent that these selected polymers be heated at a temperature usually exceeding about 65° C. and up to about 110° C., whereby they become soft, self-coherent and pliable, sufficient to be deformed and shaped as a cast or splint about a body member broken or deformed or otherwise requiring mechanical support or protection.

It was believed that similar to any normal plastic, these plastic substances would merely soften with heat and crystallize with cooling as illustrated in FIG. 9 below. For that reason, while it is indicated the product could be heated higher, such as even to 110° to 120° C., it was preferred to heat rapidly at a point just above the transition temperature and then cooled quickly only to the minimum necessary for human body tolerance, such as 50° to 55° C., a temperature just about what was believed to be the crystalline transition point, the lower limit being an extreme. However, that temperature of 50° to 60° C. is quite hot, and at the very painful limit of human body tolerance, generally too hot to be comfortable and it is usually painful to most people. It is now found that if the heating of the plastic above a minimum softening temperature exceeding the crystalline point of 55° to 60° C. variable somewhat with the history of the plastic formation and the heat treatment is for a period sufficient to thoroughly soften to convert all of the crystalline substance to its amorphous form, these specific plastic bodies go through a hysteresis range. There will be a substantial time delay upon cooling of these softened plastics before they reset to crystalline form. Thus, they may be cooled to a quite comfortable body temperature such as down to about 40° C. or less and still maintain their soft amorphous plastic characteristic for a reasonable time to slowly mount about the body member to be supported as a cast or splint at the then comfortable body temperature as stated. The formed splint placed about the body member may be held in that position even for a significant additional time period of 5 to 10 minutes before crystallizing to the rigid crystalline body supporting form in the shape into which it was deformed. A cooling curve illustrating the hysteresis is shown in FIG. 10.

In my prior copending application, Ser. No. 683,016, now U.S. Pat. No. 3,490,444, the tendency of these sheet and tape materials to develop a creep or plastic flow over substantial prolonged periods of use when so emplaced as a body member support was discovered, which is undesirable in body splint, cast or other body support member. Particularly in uses where close support is needed, the support has its tendency to lose its immediate utility as a form setting shape.

That tendency of the support to become slightly deformed in use was overcome by including reenforcing fiber materials in the plastic body. Such plastic was also improved by having its surface protected with adhesive coating members which may be applied with a pressure-sensitive adhesive for subsequent removal before use, which protects the fresh polymeric support material in unoxidized, fresh, unaged condition. Various useful coatings for that purpose are described and claimed, the further substance of the disclosure of that parent application being here incorporated by reference.

According to this invention, it is found that the plastic needs only to be heated for a period sufficient to convert all the crystalline substances to an amorphous form, and in the amorphous stage there is developed a hysteresis whereby a very substantial delay will take place in returning to the crystalline form by cooling. When the plastic is softened completely there will be a hysteresis or delay in hardening by recrystallization sufficient not only to allow the temperature to be reduced well below the temperature at which the crystalline form is stable, whereby the cooled and softened plastic may be applied as a splint or cast at a comfortable temperature to the human body, but the hysteresis will provide sufficient time delay in the recrystallization to allow the product to be comfortably molded about and shaped to the body element to be supported before substantial hardening takes place.

It is now further found according to the present invention that the plastic sheet material lying flat on the surface of a body member tends to trap moisture upon the skin of the user, which is a source of irritation, discomfort and sometimes a source of contamination of the skin surface of the encased body member. In some types of splints such as hand splints, the accumulated moisture provides a slimey irritated feeling to the user-wearer.

According to the present invention, the skin discomfort generally due to moisture is removed or reduced by several alternate structural modifications in the surface and possibly also the body of the sheet material.

In one modification, the surface may be made irregular whether by texturing, knurling, cratering with half pocks pressed or cut therein, whereby the normally smooth film of moisture on the skin is interrupted. Thereby, any liquid may seep into the surface irregularities to avoid formation on the skin of the continuous uncomfortable slimey film.

When the sheet has been reenforced with fiber so that perforation will not substantially destroy the inherent strength of the sheath plastic, then it may be perforated with close set perforations to provide the adequate porosity for substantial evoluation of moisture outward through the plastic from the skin surface.

In a third alternate, the body of the sheet may be treated with a foaming or gas-blowing agent whereby the entire sheet of plastic will foam when heated sufficient to soften it. In another procedure, one or both surfaces of the plastic are treated with a foaming agent such as by wetting the surface with a solvent, whereby upon subsequent heating to soften the sheet it develops a surface porosity or foam. Such surface porosity besides allowing escape of evolving moisture from the skin surface of the encased body member into the pores of the porous texture, also provides a comforting resiliency or softness against the skin of the body member which better conforms the support to the shape of the body member while also providing a softening, skin comforting encasement. Nevertheless, such plastic sheet is foamed, softened and set in foamed condition about the body member, whereby it provides both the absorption and/or allows escape of skin moisture and the adequate strength needed for splint reenforcement of the body member thus encased.

The invention is further described with reference to the drawings wherein.

Figure 1:
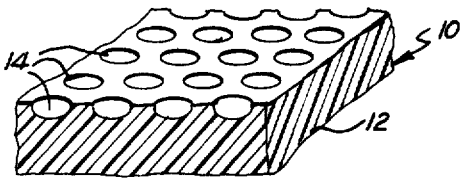
FIG. 1 shows the plastic support as sheet material formed with surface irregularities consisting of cup-like craters formed therein.
Figure 2:
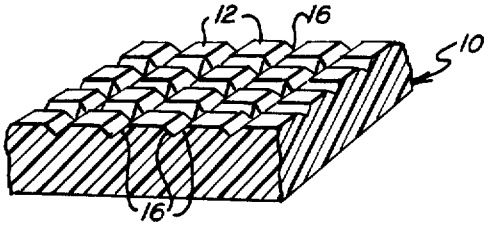
FIG. 2 shows a similar sheet material wherein the surface irregularities are knurlings.
Figure 3:
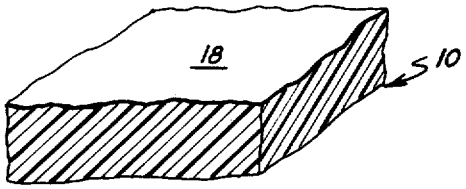
FIG. 3 shows the same sheet material wherein the surface is textured.

As shown in the drawings of FIGS. 1, 2 or 3, the surface 12 of the sheet 10 has cup-like craters 14 impressed into the softened surface, each depression forming a cavity in which moisture in contact with the skin surface will accumulate, providing both an air space and cavities to accept and store exuded moisture from the skin surface. The cup-like cavities are quite closely spaced, usually less than one quarter on center to provide optimum moisture storage capacity.

The application of the same moisture storage principle is shown in the structures of FIGS. 2 and 3. In FIG. 2 the sheet 10 has knurlings 16 cut into the surface 12 which provide grooved cavities which can occlude and store the slimey moisture. FIG. 3 provides a roughened surface 18 referred to as textured, generally formed by blowing fine, needle-like blasts of air evenly over the surface and which penetrate the softened surface sufficient to provide the moisture storage surface irregularities. A similar effect of texturing can be obtained by other methods such as pressing the softened plastic against a desirably-shaped surface such as coarse woven cloth which itself may be formed of stiffened fiber to create negative fibrous impressions within the soft plastic surface.

Figure 4:
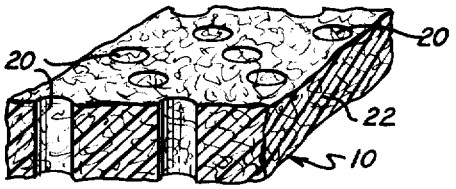
FIG. 4 illustrates fiber-reenforced plastic sheet having close perforations cut entirely through the thickness thereof.

As shown in FIG. 4, the plastic sheet 10 can be perforated with closely spaced perforations 20. The closely spaced perforations are spaced from 1/16 to ¼ inch apart and tend correspondingly to weaken the plastic sheet so that in this instance the plastic sheet will be fiber reenforced by fibers 22 incorporated within the fiber sheet, sufficient to provide the extra strength to allow the body to be perforated with perforations from about 1 to 10 percent of the volume of the body 10.

Figure 5:
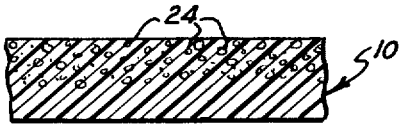
FIG. 5 illustrates the plastic sheet having one surface foamed.
Figure 7:
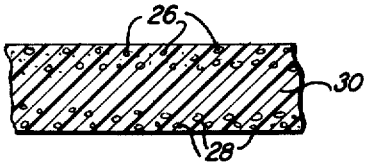
FIG. 7 illustrates a sheet in which only both opposite surfaces of the sheet are foamed.

Another desirable form of surface irregularity is to provide body pores in the sheet, such as by foaming. The foam or cellular surface is a softer resilient body contour-conforming surface which provides air spaces extending progressively from the surface in contact with the skin inward of the plastic sheet to allow absorption of moisture and a softer surface texture. Merely foaming to provide gas spaces 24 in one surface of the sheet 10, as shown in FIG. 5, may be adequate for much of this function. However, as shown in FIG. 7, it is sometimes commercially more feasible to foam both sides of the sheet 26 and 28 by dipping the polymer sheet in a solvent material which, upon subsequent heating, causes the dried sheet A to develop the pores in both surfaces 26 and 28. The center portion 30 of the plastic body does not need to contain pores and, consequently, may remain as mere sheet reenforcement.

Figure 6:
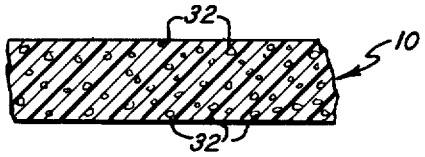
FIG. 6 illustrates the same plastic sheet wherein the entire body has been homogeneously foamed.

As shown in FIG. 6, the plastic body 10 may also be formed with pores 32 distributed homogeneously throughout the body. This may be done by forming the sheet as a foamed body so that its foamed texture is not modified in any way during conversion by softening of the sheet from sheet form to molded splint or cast form enclosing the body member.

Figure 8:
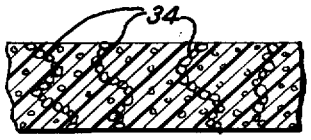
FIG. 8 illustrates a sheet wherein the foamed pores are interconnected.
Figure 9:
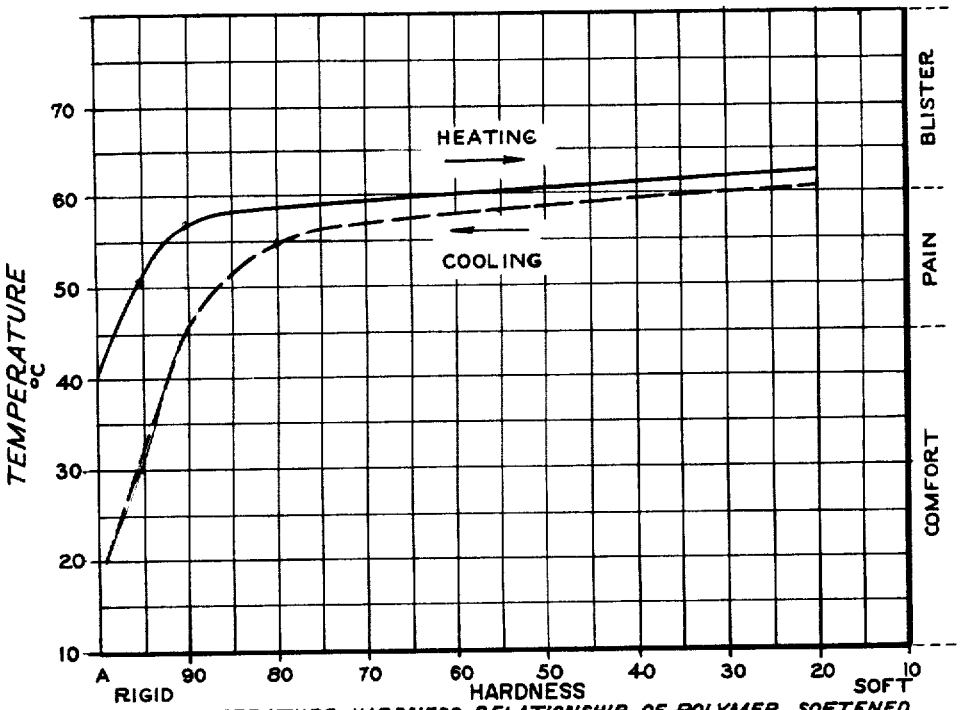
FIG. 9 illustrates that these plastic substances will merely soften with heat and crystallize with cooling.
Figure 10:
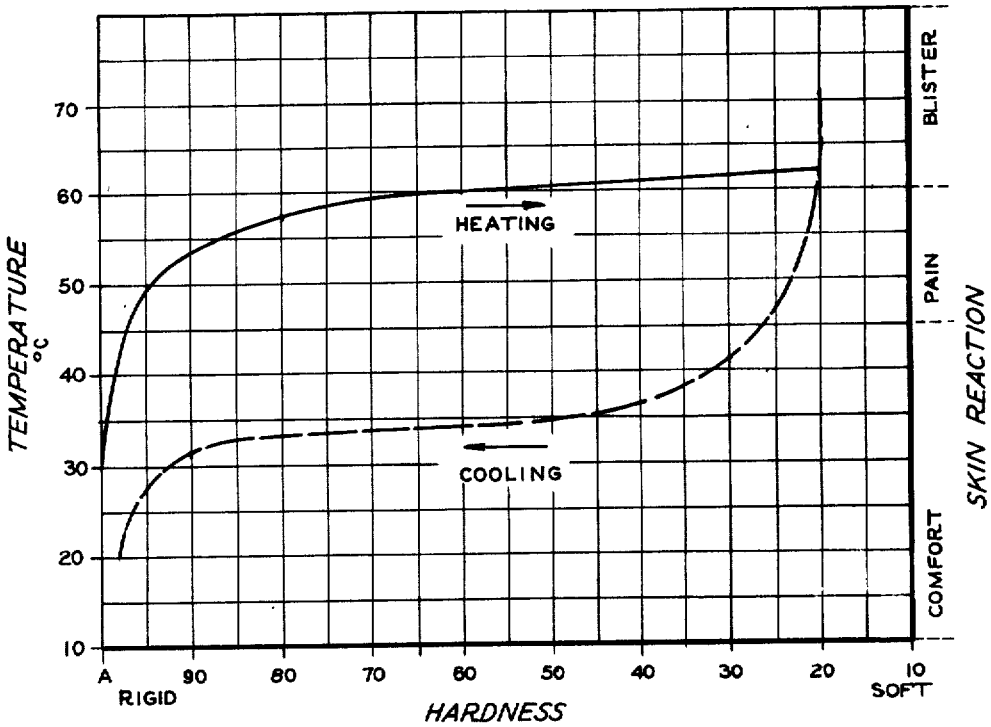
FIG. 10 illustrates the hysteresis of a cooling curve.

As shown in FIG. 8, the foamed pores may be interconnected air spaces 34 extending from surface to surface of the plastic so that the foamed body allows "breathing" to transfer moisture from the skin of the encased body member to the outside of the cast.

The invention is further described with respect to the examples which illustrate the practice of this invention:

EXAMPLE I

Precipitated balata (purified natural transpolyisoprene) is blended on a two roll mill at about 90° C. for fifteen minutes in ratio of 100 parts of polymer per 2 parts of cotten linters, 10 parts of finely-powdered titanium dioxide and one-half part of antioxidant as described in my parent application. The sheets obtained from the mill were molded in a frame to 130 mils thickness of approximately 12 inch square dimensions. The compressed sheets were then removed from the frame and perforated with one-sixteenth of an inch in diameter perforations spaced a distance of about one quarter inch, the perforations extending from surface to surface as shown in enlarged detail in FIG. 4.

In forming the splint the sheet was dipped in a water bath for a half minute at a temperature just below boiling, about 95° C., and held therein, then withdrawn and cut into a deformable pattern with a pair of scissors to correspond to the contours of the wrist and fingers to be encased. The softened sheet was then applied about the wrist and fingers and molded into place closely about each joint and bony deformation by pressing against the body member. The contiguous cut parts of the splint were cohered into a unit by slight pressure and all rough edges were removed, smoothing with slight pressure. During the formation and shaping, if a longer time is needed to effect the perfect fitting of the cast, it may be slightly rewarmed by again dipping into the hot water bath or locally heated with a warm surface or a jet of hot air. The emplaced and formed cast will set merely by holding the hand with the cast thereon quiescent for fifteen to thirty minutes, but the setting process can be accelerated by dipping the encased member in ice water. It is to be noted that the sheets can be deformed over joints by manually working with applied pressure to fit closely about the contours of bony projections, etc., and after having set with cooling to body temperature, this splint was found to be dimensionally stable, and close fitting, without irritation of bony projections typical of the hand and wrist for as long as in use. After completion and setting of the splint, undesirable edges resulting from cutting may be softened by warming the splint edges only and then manually smoothing. The splint is so permanent that it can be used for years and it is easily applied to arthritic patients where the splint may need to be fitted about a swollen hand bone projection with a good, close and delicate fit. This splint is more comfortable in the ability to transfer moisture through the close perforations, avoiding a wet clammy feeling about the encased body member while still retaining its functional body member supporting strength.

EXAMPLE II

The sheet of Example I, instead of being perforated, was knurled to form depressions in the surface of about one-thirty second of an inch depth to a surface covering as shown somewhat exaggeratedly in FIG. 2. This sheet, too, showed greatly improved comfort over a sheet having a continuous flat surface. The present example was repeated, except that the pattern was changed by impressing cups rather than knurlings as shown in FIG. 1. In a third experimental run the surface was textured as shown in FIG. 3 to produce a roughened fiber-like effect as irregularity upon the surface, again to a depth of about one-thirty second of an inch, insufficient to significantly reduce the strength of the original sheet.

EXAMPLE III

The sheets as formed in Example I are immersed in n-hexane ether for a period of fifteen minutes, withdrawn and allowed to dry in air. The products are then packaged and ready for use. Upon use the sheet is warmed in a pan of warm water at a temperature of about 85° to 100° C. and the sheet softens and simultaneously develops a foamed surface on both sides. The foam has not homogeneously penetrated into the center, a structure illustrated in FIG. 7. In its softened condition the foamed sheet is wrapped about the body member of the patient and, upon cooling, will set to a strong cast and moisture absorptive body support member of great comfort and security to the user.

Following the procedure of this Example, various solvents such as liquified petroleum gases, acetone and halogenated gases may be used as solvent, selected to avoid excessive solubility in substitution for the n-hexane, varying the temperature of the solution to adjust for the particular solubility of the plastic therein and simultaneously varying the time of immersion somewhat, merely to allow absorption of sufficient solvent in the polymer to provide for subsequent foaming upon heating. Such solvent, as stated, is evaporated to superficially dry the plastic sheet so that it may be stored until ready for use.

It is possible as shown in this example also to coat only one surface of the plastic by applying the solvent through rollers wet with the solvent, handling the plastic in continuous sheet form while maintaining the surface substantially wet by a series of rollers for a corresponding period of time. When only one surface of the sheet has been thus treated with solvent, upon subsequent warming of the sheet plastic only that treated surface will expand to porous form structure as shown in FIG. 5.

EXAMPLE IV

In a modified form as shown in FIGS. 6 and 8, the plastic in the liquid form can have a gas incorporated under high pressure and cast under high pressure with the gas trapped therein. Upon subsequent warming the sheet will expand to provide a homogeneous porous interior. It is possible that the warm gas-containing plastic can be cast in sheets of desired thickness and in porous form so that upon subsequent warming they do not foam or change in dimension in any way, since the foamed condition is already present in the sheets as they are distributed.

EXAMPLE V

Sheets as formed in Example I are soaked for two days in a saturated aqueous solution of ammonium carbonate in a closed container. They are then removed and warmed in a hot air oven using a thin glycerol layer to prevent sticking; and heated at 90° C. 760 Torr for twenty minutes. Randomly shaped and sized surface indentations are found to result on the upper side, providing modified surface texturing. The face of the sheet splints thus formed with their surface adjacent to the skin does not have the uncomfortable characteristics due to a slimey moisture accumulation as described above.

EXAMPLE VI

In a modified form as shown in FIGS. 6–8, the plastic sheet is soaked for one half hour or longer in methanol and then superficially dried by wiping. The sheets are then warmed at 90° C. for two minutes in a glycerol bath. The pressure is then reduced to less than 10 mm Torr at 90° C. for ten minutes. The sheets are then cooled at atmospheric pressure. The resultant product had about one hundred porous openings in the surface per square inch of surface and provided direct void channels between the surfaces. Repetition of soaking and evaporation increases the porosity at a controllable rate. The resulting open foam structure can be softened by warming in water near the boiling point and formed into a rugged cast about a fractured or injured body member. It can be so retained in protective support for long periods of time without discomfort due to odor or moisture collection. Areas of discomfort due to chaffing, resulting from alterations of body contours on healing, can be rectified by warming isolated locations with a hot surface, such as a heat sealer commonly used in plastic packaging. A wrapper splint may be cut longitudinally with a common orthopedic rotary saw while cold, opened like a bivalve and converted to a removable splint without altering its contour-fitting qualities. The bivalve clam-like splint can be kept closed with exterior tapes, etc., as needed.

EXAMPLE VII

A solid sheet of plastic corresponding to that described in Example I is similarly made except that the polymer is low temperature polymerized polychloroprene. The sheet in an unaged condition is then soaked for several days in diethyl ether and foamed, after superficial drying, by heating for ten minutes in boiling water. The resultant product has a cellular structure and surface pores which improve its value as a splinting material. It is found that this product is useful for many static hand splints but needs external support in splints encountering stress such as in "cock up" splints for spastic wrists. It is preferred that the sheet for foaming be freshly prepared or that the surface be protected as described in my copending application.

EXAMPLE VIII

Example VII is repeated with a polymer sheet made as in Example I except that the plastic sheet contains fifty parts of transpolyisoprene or fifty parts of transpolychloroprene. The results obtained are similar with the product requiring external support in certain cases as described above, although the inclusion of ¼ inch fibers in quantity of one part as in my original composition greatly increases its strength, making it possible to use this as a cast for large fractures.

While as stated in Example I the sheets may contain reenforcing fiber, whatever the surface configuration, and that fiber will be necessary only where substantial perforation is applied, the fiber can be omitted with, however, some sacrifice of inherent strength including reduced tendency of the polymer sheet to creep when applied as a splint about a body member.

In applying the said sheet material, it may be warmed in a hot water bath sufficient to soften it. Where the sheet material includes a gas forming agent, it becomes foamy when warmed. The warming temperature usually is less than 110° C., but always is above the body temperatures, such as above 60° C., which is sufficient to activate the foaming agent for developing a foam in one or both surfaces, and sometimes throughout the entire body of the sheet material. Such sheets may be quite thin, having a thickness as low as 2 mils, ranging upward to 200 mils. However, it is most usual for body support to use a sheet having a thickness in the range of 100 to 150 mils. Upon warming, the sheet material becomes softened in a few minutes, sufficient to deform the entire sheet about the body member to be encased. It may be cut with a pair of scissors to the desired pattern or splint or protective cast as needed for the particular member to be supported. It is pressed about the body member for comfortable support with the surface having the irregularities or foam disposed adjacent to the skin of the body member being encased. The softened edges with firm pressure will cohere to each other, but the edges of the sheet may be slightly rewarmed as needed for improving the adhesion after assembling the sheet about the body member, if this is found to be necessary.

Other improvements as described and claimed in my parent application including desirable coatings may be used with the surface modified sheets thereof.

What is claimed is:

1. A process of forming a body supporting member such as a cast, splint or the like, comprising warming a sheet of crystalline thermoplastic polymer having a thickness in the range of about 2 to 200 mils, to a temperature in the range of about 60° to 110° C. for a heat softening period sufficient to convert the total crystalline substance to a softened, amorphous form, said heat-softened sheet of polymer developing a hysteresis to have a setting time substantially delayed to remain soft and amorphous below the crystalline setting temperature, whereby it may be cooled to a comfortable body temperature below about 40° C., whereby the sheet may be formed and shaped for use as a body supporting cast or splint, [said sheet having at least its surface adjacent to the body member to be protected deformed to include surface irregularities capable of absorbing and interrupting continuous moisture films that may be developed upon the body member to be protected, said surface irregularities consisting of cup-like depressions, knurled depressions, texturing, foam and close spaced perforations which are evenly distributed throughout the surface of the said plastic and the like,] cutting said softened sheet to dimensional size and manually shaping, wrapping and forming said sheet [upon] *at a comfortable body temperature in the form of* the body member to be supported [and protected at said comfortable body temperature with the surface irregularities disposed adjacent to the body member enclosed,] and maintaining the entire supported assembly substantially immobile until the sheet sets by crystallization to a rigid body support.

2. A process of forming a body supporting member such as a cast, splint or the like, comprising warming a sheet of polymer consisting of a conjugated diolefine compound having a thickness in the range of about 2 to 200 mils, setting by crystallization at temperatures below about [50° C.] *40° C.* and being heat softened and pliable at raised temperatures in the range of 60° C. to 110° C., said sheet having a hysteresis whereby it may be cooled substantially below its normal crystallization point, to lower temperature in a comfortable contact with a body member at a temperature below about 40° C., whereby it may be heat softened, deformed and shaped for use as a body supporting medical cast or splint, said sheet having at least its surface adjacent to the body member to be protected deformed to include surface irregularities capable of absorbing and interrupting continuous moisture films that may be developed upon the body member to be protected, said surface irregularities consisting of cup-like depressions, knurled depressions, texturing, foam and [closed space] perforations which are evenly distributed throughout the surface of said plastic and the like, cutting said softened sheet to dimensional size and manually shaping, wrapping and forming said sheet upon the body member to be supported and protected at said comfortable body temperature with the surface irregularities disposed adjacent to the body member [enclosed], and maintaining the entire supported assembly substantially immobile until the sheet sets by crystallization to a rigid body support.

3. A process of forming a body supporting member such as a cast, splint or the like, comprising warming a sheet of crystalline thermoplastic polymer selected from the group consisting of transpolyisoprene and transpolychloroprene having a thickness in the range of about 2 to 200 mils, to a temperature in the range of about 60° C. to 110° C. for a heat softening period sufficient to convert the total crystalline substance to a softened amorphous form, said heat softened sheet of polymer developing a hysteresis to have a setting time substantially delayed to remain soft and amorphous well below the crystalline setting temperature, whereby it may be cooled to a comfortable body temperature without immediately setting, cooling said heat softened plastic sheet to a comfortable body temperature below about 40° C., whereby the sheet may be formed and shaped for use as a body supporting cast or splint, said sheet having at least its surface adjacent to the body member to be protected deformed to include surface irregularities capable of absorbing and interrupting continuous moisture films that may be developed upon the body member to be protected, said surface irregularities consisting of cup-like depressions, knurled depressions, texturing, foam and close spaced perforations which are [evenly] distributed throughout the surface of said plastic and the like, cutting said softened sheet to dimensional size and manually shaping, wrapping and forming said sheet upon the body member to be supported and protected at said comfortable body temperature with the surface irregularities disposed adjacent to the body member [enclosed], and maintaining the entire supported assembly substantially immobile until the sheet sets by crystallization to a rigid body support.

4. The process as defined in claim 2 wherein the sheet material has surface irregularities comprising a foamy texture formed by generation of gases in the sheet material adjacent to at least one surface prior to applying said sheet material to the body member to be supported.

5. The process as defined in claim 2 wherein the surface irregularities comprise foam formed by generation of gases extending throughout the body of said sheet material from surface to surface prior to applying said sheet material to the body member to be supported.

6. The process as defined in claim 2 wherein the sheet material includes a foaming agent activatable with heat so that upon warming said sheet material for softening sufficient to apply the said material as a body support member the foaming agent is simultaneously activated to convert at least one surface of the sheet material to a foamy mixture prior to applying said sheet material to the body member to be supported.

* * * * *